(12) United States Patent
Connor et al.

(10) Patent No.: US 7,980,141 B2
(45) Date of Patent: Jul. 19, 2011

(54) WEARABLE POSITION OR MOTION SENSING SYSTEMS OR METHODS

(75) Inventors: Robert A. Connor, Minneapolis, MN (US); Jon K. Moon, Edina, MN (US)

(73) Assignee: Robert Connor, Minneapolis, MN (US)

( * ) Notice: Subject to any disclaimer, the term of this patent is extended or adjusted under 35 U.S.C. 154(b) by 355 days.

(21) Appl. No.: 12/080,164

(22) Filed: Apr. 1, 2008

(65) Prior Publication Data
US 2009/0025483 A1 Jan. 29, 2009

Related U.S. Application Data

(60) Provisional application No. 60/962,296, filed on Jul. 27, 2007.

(51) Int. Cl.
*G01N 3/20* (2006.01)
(52) U.S. Cl. .......................................................... 73/849
(58) Field of Classification Search ...................... 73/849
See application file for complete search history.

(56) References Cited

U.S. PATENT DOCUMENTS

| | | |
|---|---|---|
| 3,974,491 A | 8/1976 | Sipe |
| 4,542,291 A | 9/1985 | Zimmerman |
| 5,012,819 A | 5/1991 | Marras et al. |
| 5,086,785 A | 2/1992 | Gentile et al. |
| 5,125,412 A | 6/1992 | Thornton |
| 5,152,293 A * | 10/1992 | Vonesh et al. .................. 600/459 |
| 5,184,009 A | 2/1993 | Wright et al. |
| 5,184,319 A | 2/1993 | Kramer |
| 5,203,340 A * | 4/1993 | Gustafson et al. ............. 600/488 |
| 5,280,265 A | 1/1994 | Kramer et al. |
| 5,337,758 A | 8/1994 | Moore et al. |
| 5,375,610 A | 12/1994 | LaCourse et al. |
| 5,442,729 A | 8/1995 | Kramer et al. |
| 5,474,083 A | 12/1995 | Church et al. |
| 5,533,531 A | 7/1996 | Edwards et al. |
| 5,592,401 A | 1/1997 | Kramer |
| 5,676,157 A | 10/1997 | Kramer |
| 5,694,497 A | 12/1997 | Sansone |
| 5,791,231 A * | 8/1998 | Cohn et al. ......................... 92/88 |

(Continued)

OTHER PUBLICATIONS

"Animazoo—3D Motion Capture Equipment: Gypsy Products from Animazoo", [online]. © 2004 Animazoo. [retrieved Jul. 16, 2007]. Retrieved from the Internet: <URL: http://www.animazoo.com/products/index.htm>, 1 pg.

(Continued)

*Primary Examiner* — Lisa M Caputo
*Assistant Examiner* — Octavia Davis
(74) *Attorney, Agent, or Firm* — Schwegman, Lundberg & Woessner, P.A.

(57) ABSTRACT

A wearable system of one or more body position or motion sensors can include a flexible sensing element to be coupled to or worn on a body. When straight, the flexible sensing element defines a longitudinal axis. It includes a lumen carrying a flowable substance, such as a liquid, gas, or gel. A measurable parameter of the flowable substance, such as pressure, volume, or flow, provides an indication of a longitudinal axial bending, twisting, or elongation, such as due to movement of at least one body part to which the sensing element is coupled. The lumen is coupled to a transducer by at least one conduit for the flowable substance. The transducer converts the measurable parameter of the flowable substance into a transducer output signal indicative of the longitudinal axial bending, twisting, or elongation of the sensing element, from which body part position or movement information can be derived.

28 Claims, 6 Drawing Sheets

U.S. PATENT DOCUMENTS

| | | | |
|---|---|---|---|
| 5,930,741 | A | 7/1999 | Kramer |
| 5,961,541 | A * | 10/1999 | Ferrati ............................ 607/49 |
| 5,980,472 | A * | 11/1999 | Seyl ................................ 600/587 |
| 6,005,548 | A | 12/1999 | Latypov et al. |
| 6,032,530 | A | 3/2000 | Hock |
| 6,050,962 | A | 4/2000 | Kramer et al. |
| 6,059,576 | A | 5/2000 | Brann |
| 6,119,516 | A | 9/2000 | Hock |
| 6,127,672 | A | 10/2000 | Danisch |
| 6,142,982 | A * | 11/2000 | Hunt et al. ..................... 604/313 |
| 6,162,190 | A | 12/2000 | Kramer |
| 6,165,143 | A | 12/2000 | van Lummel |
| 6,210,301 | B1 | 4/2001 | Abraham-Fuchs et al. |
| 6,341,504 | B1 | 1/2002 | Istook |
| 6,360,615 | B1 | 3/2002 | Smela |
| 6,428,490 | B1 | 8/2002 | Kramer et al. |
| 6,563,107 | B2 | 5/2003 | Danisch et al. |
| 6,640,202 | B1 | 10/2003 | Dietz et al. |
| 6,673,027 | B2 | 1/2004 | Fischer |
| 6,703,939 | B2 | 3/2004 | Lehrman et al. |
| 6,733,464 | B2 * | 5/2004 | Olbrich et al. ................. 600/538 |
| 6,834,436 | B2 | 12/2004 | Townsend et al. |
| 6,864,796 | B2 | 3/2005 | Lehrman et al. |
| 6,940,062 | B2 | 9/2005 | Kwon et al. |
| 7,070,571 | B2 | 7/2006 | Kramer et al. |
| 7,087,075 | B2 * | 8/2006 | Briscoe et al. ................. 607/104 |
| 7,149,584 | B1 | 12/2006 | Koh et al. |
| 7,292,151 | B2 * | 11/2007 | Ferguson et al. ........... 340/573.1 |
| 7,328,070 | B2 * | 2/2008 | Gerber et al. .................... 607/41 |
| 7,572,228 | B2 * | 8/2009 | Wolinsky et al. .............. 600/486 |
| 7,572,253 | B2 * | 8/2009 | Gotani ................................ 606/1 |
| 7,602,310 | B2 * | 10/2009 | Mann et al. ............... 340/870.07 |
| 2001/0003712 | A1 | 6/2001 | Roelofs |
| 2001/0020140 | A1 | 9/2001 | Kramer |
| 2003/0045816 | A1 | 3/2003 | Foxlin |
| 2005/0106977 | A1 | 5/2005 | Coulston |
| 2005/0118914 | A1 * | 6/2005 | Kuo et al. ....................... 442/301 |
| 2006/0022833 | A1 | 2/2006 | Ferguson et al. |
| 2006/0064039 | A1 * | 3/2006 | Griego et al. ................. 600/587 |
| 2006/0070443 | A1 | 4/2006 | Pristup |
| 2006/0144213 | A1 | 7/2006 | Mann |
| 2006/0147678 | A1 * | 7/2006 | Marmaropoulos et al. ... 428/172 |
| 2006/0189899 | A1 | 8/2006 | Flaherty et al. |
| 2006/0210112 | A1 | 9/2006 | Cohen et al. |
| 2006/0212097 | A1 | 9/2006 | Varadan et al. |
| 2006/0238490 | A1 | 10/2006 | Stanley et al. |
| 2006/0241520 | A1 | 10/2006 | Robertson |
| 2006/0241521 | A1 | 10/2006 | Cohen |
| 2006/0282017 | A1 | 12/2006 | Avni et al. |

OTHER PUBLICATIONS

"Ascension Products—Flock of Birds®", [online]. [retrieved Jul. 16, 2007]. Retrieved from the Internet: <URL: http://www.ascension-tech.com/products/flockofbirds.php>, 2 pgs.

"Biometrics Ltd Research—Goniometers and Torsiometers", [online]. [retrieved Jul. 16, 2007]. Retrieved: http://www.biometricsltd.com/y%20gonio.htm>, 2 pgs.

"Biopac—TSD130A / Twin Axis Goniometer, 110mm", [online]. [retrieved Jul. 16, 2007]. Retrieved from the Internet: <URL: http://www.biopac.com/Research.asp?Pid=3695&Main=Transducers>, 1 pg.

"Codamotion Products—Hardware and Software", [online]. [retrieved Jul. 16, 2007]. Retrieved from the Internet: <URL: http://www.charndyn.com/Products/Products_Intro.html>, 1 pg.

"Greenleaf Products", [online]. [retrieved Jul. 16, 2007]. Retrieved from the Internet: <URL: http://www.greanleafmed.com/products.htm>, 1 pg.

"High Performance Real-Time 3D Motion Capture Systems for Professionals", [online]. © 1997-2007 Phoenix Technologies Inc. [retrieved Jul. 16, 2007]. Retrieved from the Internet: <URL: http://www.ptiphoenix.com/Products.php>, 1 pg.

"Immersion Corporation—3D Interaction", [online]. © 2007 Immersion Corporation. [retrieved Jul. 16, 2007]. Retrieved from the Internet: <URL: http://www.immersion.com/3d/>, 1 pg.

"Liberty™ Latus™ Wireless Motion Tracking System from Polhemus", [online]. [retrieved Jul. 16, 2007]. Retrieved from the Internet: <URL:. http://www.polhemus.com/?page=Motion_Liberty_Latus>, 2 pgs.

"Measurand—Motion Capture for the Classroom", [online]. [retrieved Jul. 16, 2007]. Retrieved from the Internet: <URL: http://www.measurand.com>, 1 pg.

"Meta Motion—Motion Capture Hardware—Face Trackers", [online]. © 2006 Meta Motion. [retrieved Jul. 16, 2007]. Retrieved from the Internet: <URL: http://www.metamotion.com/hardware/motion-capture-hardware.htm>, 1 pg.

"MicroStrain® Inclinometers: Orientation Sensors", [online]. [retrieved Jul. 16, 2007]. Retrieved from the Internet: <URL: http://www.microstrain.com/inclinometers.aspx>, 1 pg.

"Mikromak Service Brinkmann—Human Motion", [online]. © Mikromak Service Brinkmann. [retrieved Jul. 16, 2007]. Retrieved from the Internet: http://www.mikromak.com/en/en_menschl_beweg.htm>, 1 pg.

"MiniSun—Ideea Information", [online]. © MiniSun 2000-2007. [retrieved Jul. 16, 2007]. Retrieved from the Internet: <URL: http://www.minisun.com/ideea.asp>, 1 pg.

"Motek Medical", [online]. [archived Jul. 8, 2007]. Retrieved from the Internet: <URL: http://web.archive.org/web/20070708132130/http://www.e-motek.com/medical/index.htm>, 2 pgs.

"Motion Lab Systems, Inc.", [online]. © 1995-2007 Motion Lab Systems, Inc. [retrieved 2007]. Retrieved via the Internet: <URL:http://www.emgsrus.com>, 2 pgs.

"MotionAnalysis—Movement Analysis Products", [online]. © 2007 Motion Analysis Corporation. [retrieved Jul. 16, 2007]. Retrieved from the Internet: <URL: http://www.motionanalysis.com/applications/movement/movementproducts.html>, 1 pg.

"NCHS Study—Prevalence of Overweight and Obesity Among Adults: United States, 1999-2002", [online]. [retrieved Mar. 28, 2008]. Retrieved from the Internet: <URL: http://www.cdc.gov/nchs/products/pubs/pubd/hestats/obese/obse99.htm>, (2007), 3 pgs.

"NDI: The Aurora Electromagnetic Measurement System", [online]. © 2007 Northern Digital Inc. [retrieved Jul. 16, 2007]. Retrieved from the Internet: <URL: http://www.ndigital.com/medical/aurora.php>, 1 pg.

"noDNA—Sensoric Systems", [online]. [retrieved Jul. 16, 2007]. Retrieved from the Internet: <URL: http://www.nodna.com/index.php?id=7&L=1>, 1 pg.

"Noraxon—Manufacturers of Professional Surface Electromyography Products", [online]. [retrieved Jul. 16, 2007]. Retrieved from the Internet: <URL: http://www.noraxon.com/index.php3>, 1 pg.

"PA-06-055: Bioengineering Approaches to Energy Balance and Obesity", [online]. [retrieved Mar. 18, 2008]. Retrieved from the Internet: <URL: http://grants.nih.gov/grants/guide/pa-files/PA-06-055.html>, 22 pgs.

"PhaseSpace Inc. / Optical Motion Capture", [online]. [retrieved Jul. 16, 2007]. Retrieved from the Internet: <URL: http://www.phasespace.com/hardware.html>, 2 pgs.

"Qualisy Motion Capture", [online]. [retrieved Mar. 31, 2008]. Retrieved from the Internet: <URL: http://www.qualisys.com/templates/Q01.asp?sida=34>, 1 pg.

"Vicon / Products—Cameras", [online]. [retrieved Jul. 16, 2007]. Retrieved via the Internet: <URL: http://www.vicon.com/products/cameras.html>, 1 pg.

"Vista Medical—Store", [online]. [retrieved Jul. 16, 2007]. Retrieved from the Internet: <URL: http://www.pressuremapping.com/index.cfm?pageID=13&section=9>, 1 pg.

"VivoMetrics®—Sports & Fitness—Product Line", [online]. © 2007 VivoMetrics. [retrieved Jul. 16, 2007]. Retrieved from the Internet: <URL: http://www.vivometrics.com/sport/view_our_products/product_line.php>, 2 pgs.

"Xsen Motion Technologies—Moven-Inertial Motion Capturing", [online}. © 2007 Xsens Motion Technologies. [archived Jul. 17, 2007]. Retrieved from the Internet: <URL: http://web.archive.org/web/20070717123324/www.xsens.com/index.php?mainmenu=products&submenu=human_motion&subsubmenu=Moven>, 2 pgs.

Deyo, R. A., et al., "Back Pain Prevalence and Visit Rates: Estimates From U.S. National Surveys, 2002", [online]. [retrieved Mar. 28, 2008]. Retrieved from the Internet: <URL: http://ovidsp.tx.ovid.com.floyd.lib.umn.edu/spa/ovidweb.cgi>, 5 pgs.

Gibbs, P. T., et al., "Wearable Conductive Fiber Sensors for Multi-Axis Human Joint Angle Measurements", [online]. [retrieved Jul. 16, 2007]. Retrieved from the Internet: <URL: http://www.pubmedcentral.nih.gov/articlerender.fcgi?artid=555561>, 15 pgs.

Huddleston, J., et al., "Ambulatory Measurement of Knee Motion and Physical Activity: Preliminary Evaluation of a Smart Activity Monitor", [online]. [retrieved Mar. 28, 2008]. Retrieved from the Internet: <URL: http://www.jneuroengrehab.com/content/3/1/21>, 6 pgs.

* cited by examiner

WEARABLE POSITION OR MOTION SENSING SYSTEMS OR METHODS

RELATED APPLICATION(S)

This patent application claims the benefit of priority under 35 U.S.C. § 119(e) to U.S. Provisional Application Ser. No. 60/962,296, filed on Jul. 27, 2007, which is incorporated herein by reference.

TECHNICAL FIELD

This document pertains generally to position, posture, gait, or motion sensing of a human or animal body, and more particularly, but not by way of limitation, to wearable position or motion sensing systems and methods.

BACKGROUND

There are many potential applications that can benefit from recognizing position, posture, gait, or motion of a human or animal body. Examples of such potential applications include, among other things, medicine (e.g., gait analysis, exercise measurements, telemedicine), entertainment (e.g., animation, virtual reality, gaming, live performance), sports (e.g., training, virtual sports), education, communication, military, and product development.

OVERVIEW

This document describes, among other things, a wearable system of one or more body position or motion sensors. In certain examples, such a sensor can include a flexible sensing element that is configured to be coupled to or worn on a human or animal body. For example, the flexible sensing element can be taped to the body or integrated into a garment that can be worn on the body. The flexible sensing element can include a flexible elongate member that, when straight, defines a longitudinal axis. The elongate member includes a lumen carrying a flowable substance, such as a liquid, gas, or gel. A measurable parameter of the flowable substance, such as pressure, volume, or flow, provides an indication of a longitudinal axial bending, twisting, or elongation, such as due to movement of at least one body part to which the sensing element is coupled. The lumen can be coupled to a transducer by at least one conduit for the flowable substance. The transducer converts the measurable parameter of the flowable substance into a transducer output signal (such as an electrical or optical signal) which is indicative of the longitudinal axial bending, twisting, or elongation of the sensing element. Based on the transducer output signal, body part position or movement information can be provided to a user, device, or process. Some examples are described below, however, this should not be considered an exhaustive list.

Example 1 describes an apparatus. In this example, the apparatus includes a flexing sensing element, configured to be coupled to or worn on a human or animal body, the sensing element providing an indication of a longitudinal axial bending, twisting, or elongation due to movement of at least one body part, the sensing element comprising a flexible elongate member, the flexible elongate member comprising a lumen carrying a flowable substance comprising at least one of a liquid, a gas, or a gel. A transducer is in flowable substance communication with the lumen of the sensing element. The transducer is configured to transduce an indication of the longitudinal axial bending, twisting, or elongation of the sensing element into at least one output indication of body part movement to be provided to a user or a device.

In Example 2, the apparatus of Example 1 optionally comprises a plurality of the flexing sensing elements, comprising a first sensing element and a second sensing element, the first and second sensing elements comprising respective flexible elongate members comprising respective lumens carrying the flowable substance. A plurality of the transducers respectively are in flowable communication with the first and second sensing elements. The transducer is configured to transduce indications of the longitudinal axial bending, twisting, or elongation of the first and second sensing elements into the at least one output indication of body part movement.

In Example 3, the apparatus of any one or more of Examples 1-2 optionally comprises a garment with which the first and second sensing elements are integrated.

In Example 4, the apparatus of any one or more of Examples 1-3 optionally comprises a compressive fabric to hold the first and second sensing elements against the body.

In Example 5, the apparatus of any one or more of Examples 1-4 optionally comprises the first sensing element being generally parallel to the second sensing element.

In Example 6, the apparatus of any one or more of Examples 1-4 optionally comprises the first sensing element being generally orthogonal to the second sensing element.

In Example 7, the apparatus of any one or more of Examples 1-6 optionally comprises the flowable substance being a gas.

In Example 8, the apparatus of any one or more of Examples 1-7 optionally comprises a coupling device, configured to couple the sensing element to the body.

In Example 9, the apparatus of any one or more of Examples 1-8 optionally comprises the transducer being configured to transduce an indication of at least one of flow, volume, or pressure of the flowable substance, arising from the longitudinal axial bending, twisting, or elongation of the sensing element, into an electrical or optical signal representing the indication of body part movement.

In Example 10, the apparatus of any one or more of Examples 1-9 optionally comprises at least one flowable substance conduit, coupled to the lumen, wherein the transducer is in flowable substance communication with the lumen via the conduit, and the at least one conduit and the sensing element being configured such that the transducer is less sensitive to the longitudinal axial bending, twisting, or elongation of the at least one conduit than to the corresponding longitudinal axial bending, twisting, or elongation of the sensing element.

In Example 11, the apparatus of any one or more of Examples 1-10 optionally comprises the transducer being configured to transduce an indication of pressure of the flowable substance, arising from the longitudinal axial bending, twisting, or elongation of the sensing element, into an electrical signal representing the indication of body part movement.

In Example 12, the apparatus of any one or more of Examples 1-11 optionally comprises the sensing element being inflatable.

In Example 13, the apparatus of any one or more of Examples 1-12 optionally comprises the first sensing element and the at least one conduit forming a flowable substance conduction loop.

In Example 14, the apparatus of any one or more of Examples 1-13 optionally is configured such that the lumen comprises a diameter of less than 1 inch.

In Example 15, the apparatus of any one or more of Examples 1-14 optionally comprises the lumen comprises a diameter of less than 1 millimeter.

In Example 16, the apparatus of any one or more of Examples 1-15 optionally comprises a number of sensing elements that is selected to represent movement of joints distributed throughout the body.

In Example 17, the apparatus of any one or more of Examples 1-16 is configured such that at least a portion of the sensing element comprises multiple braided, woven, or twisted strands.

Example 18 describes a method comprising: sensing a longitudinal axial bending, twisting, or elongation of a flexible elongate member sensing element that is coupled to or worn on a human or animal body, the sensing including using a flowable substance carried by a lumen of the flexible elongate member, the flowable substance comprising at least one of a liquid, a gas, or a gel; and transducing an indication of the longitudinal axial bending, twisting, or elongation of the sensing element into at least one output indication of body part movement to be provided to a user or a device.

In Example 19, the method of Example 18 optionally comprises: sensing a longitudinal axial bending, twisting, or elongation of a plurality of the flexible elongate member sensing elements comprising a first sensing element and a second sensing element; and communicating the flowable substance from the plurality of the flexible elongate member sensing elements to at least one transducer is in flowable communication with at least one of the first and second sensing elements for performing the transducing.

In Example 20, the method of any one or more of Examples 18-19 optionally comprises sensing using first and second sensing elements that are generally located in parallel to each other.

In Example 21, the method of any one or more of Examples 18-19 optionally comprises sensing using first and second sensing elements that are generally located orthogonal to each other.

In Example 22, the method of any one or more of Examples 18-21 optionally comprises sensing a flow or volume of the flowable substance.

In Example 23, the method of any one or more of Examples 18-22 optionally comprises sensing a pressure of the flowable substance.

In Example 24, the method of any one or more of Examples 18-23 optionally comprises sensing using at least one of a braided, woven, or twisted flexible elongate member.

Example 25 describes an apparatus comprising: means for sensing a longitudinal axial bending, twisting, or elongation of a flexible elongate member sensing element that is coupled to or worn on a human or animal body, the sensing including using a flowable substance carried by a lumen of the flexible elongate member, the flowable substance comprising at least one of a liquid, a gas, or a gel; and means for transducing an indication of the longitudinal axial bending, twisting, or elongation of the sensing element into at least one output indication of body part movement to be provided to a user or a device.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

This document describes, among other things, a wearable system of one or more body position or motion sensors. In certain examples, such a sensor can include a flexible sensing element that is configured to be coupled to or worn on a human or animal body. For example, the flexible sensing element can be taped to the body or integrated into a garment that can be worn on the body. The flexible sensing element can include a flexible elongate member that, when straight, defines a longitudinal axis. The elongate member includes a lumen carrying a flowable substance, such as a liquid, gas, or gel. A measurable parameter of the flowable substance, such as pressure, volume, or flow, provides an indication of a longitudinal axial bending or twisting, such as due to movement of at least one body part to which the sensing element is coupled. The lumen can be coupled to a transducer by at least one conduit for the flowable substance. The transducer converts the measurable parameter of the flowable substance into a transducer output signal (such as an electrical or optical signal) which is indicative of the longitudinal axial bending or the twisting of the sensing element. Based on the transducer output signal, body part position or movement information can be provided to a user, device, or process.

Figure 1:
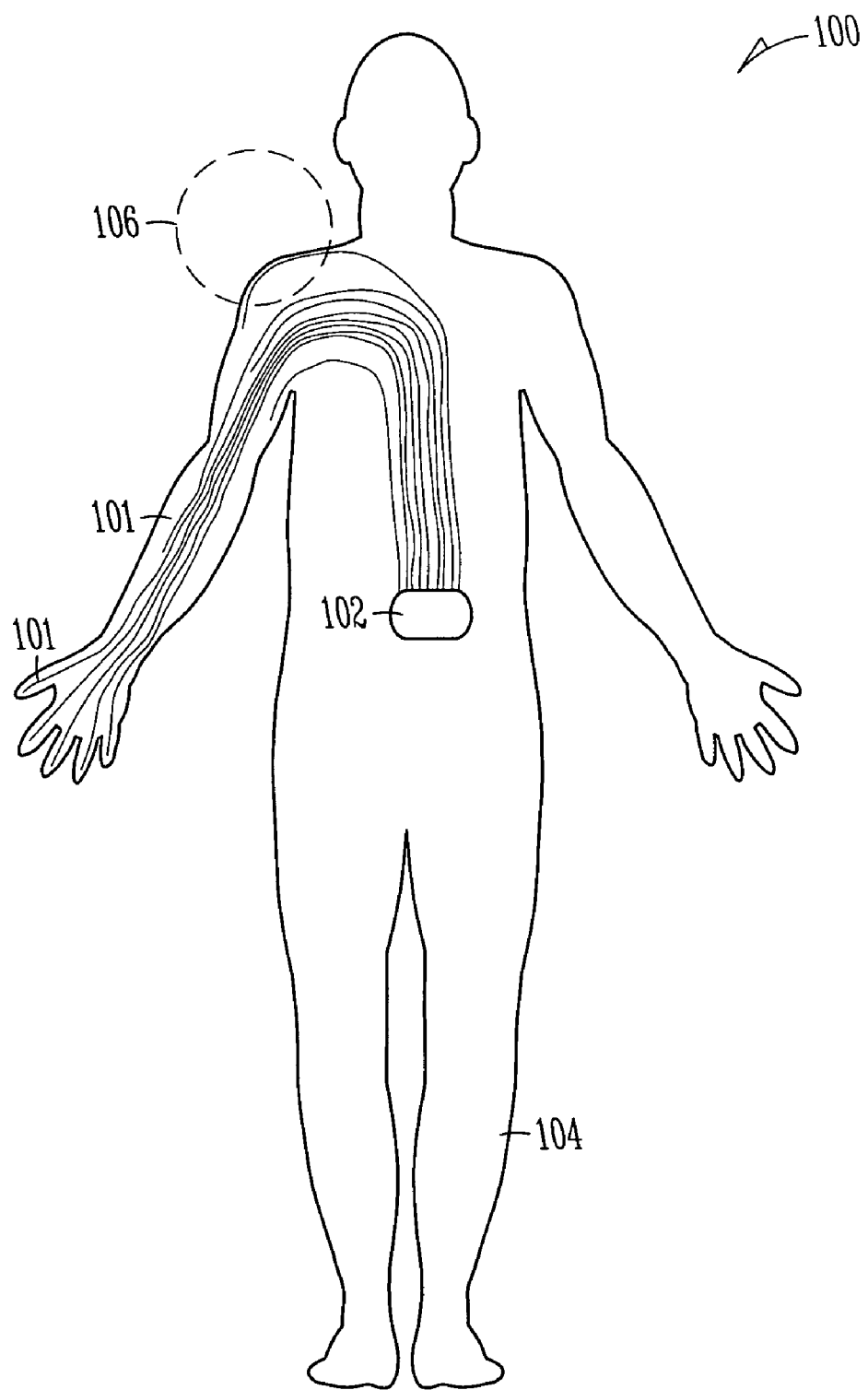
FIG. 1 is a schematic drawing illustrating generally an example of portions of a body position or motion detection system and portions of an environment with which it is used.

FIG. 1 is a schematic drawing illustrating generally an example of portions of a body position or motion detection system 100 and portions of an environment with which it is used. In this illustrative example, one or more flexible tubes 101, are located across the top and front of the right shoulder, across the front of the right elbow, and across the front of the right hand, such as extending along the fingers toward the fingertips. The tubes 101 are filled with a flowable substance, such as a gas, liquid, gel, or the like. In this example, the tubes 101 can sense body motion or position by providing flexible sensing elements that span respective joints, such as a right shoulder, a right elbow, or a right hand. The tubes 101 can also include non-sensing elements, for example, respective conduits that communicate the flowable substance from respective flexible sensing elements toward an ambulatory transducer unit 102 at which proximal ends of the tubes 101 generally converge. In this illustrative example, the ambulatory transducer unit 102 is located on the abdomen of the person 104 to which the tubes 101 are coupled, such as by corresponding individual or collective snap-couplings or the like that permit user connection or disconnection of the tubes 101 from the ambulatory transducer unit. However, the ambulatory transducer unit 102 could be located elsewhere on the person 104, if desired.

The ambulatory transducer unit 102 generally includes at least one transducer that converts a measurable parameter of the flowable substance (e.g., pressure, volume, flow, or the like) into at least one corresponding transducer output signal (such as an electrical or optical signal) which is indicative of the longitudinal axial bending or the twisting of the sensing element. The at least one transducer output signal is communicated to a processor circuit, which can be included in the ambulatory transducer unit 102, or can be located away from the person 104 but communicatively coupled to the ambulatory transducer unit 102, such as via wired or wireless communication with a communication circuit of the ambulatory transducer unit 102. The processor circuit processes the at least one transducer output signal to generate body position or motion information about the person 104, such as for use in one or more of various applications, such as described above.

In the interest of illustrative clarity, the example shown in FIG. 1 does not show a large number of tubes 101. However, more similar tubes 101 could be added elsewhere on the person 104, such as on the left side of the person 104, on the lower left or right portions of the person 104, on the back of the person 104, and so forth. In a full-body example, there can be enough independent sensing segments spanning each joint of interest to measure a wide range of motion for that joint of interest.

In the interest of illustrative clarity, the example shown in FIG. 1 shows one tube 101 located along each finger on the right hand. In certain such examples, there is only one flexible sensing element spanning all three joints for each finger. In other examples, however, there is a separate tube 101 and flexible sensing element for each joint of each finger. As microfluidic technology advances, a high degree of motion recognition precision can be obtained, such as by integrating many microtubes into a wearable garment, which can also be made washable. The garment can be made of an elastic or other resilient fabric material (e.g., Lycra® or other elastane or spandex material), such that the fabric provides a compressive force to hold one or more of the flexible sensing elements against the body of the person 104, such as in place spanning a joint of interest.

Figure 2:
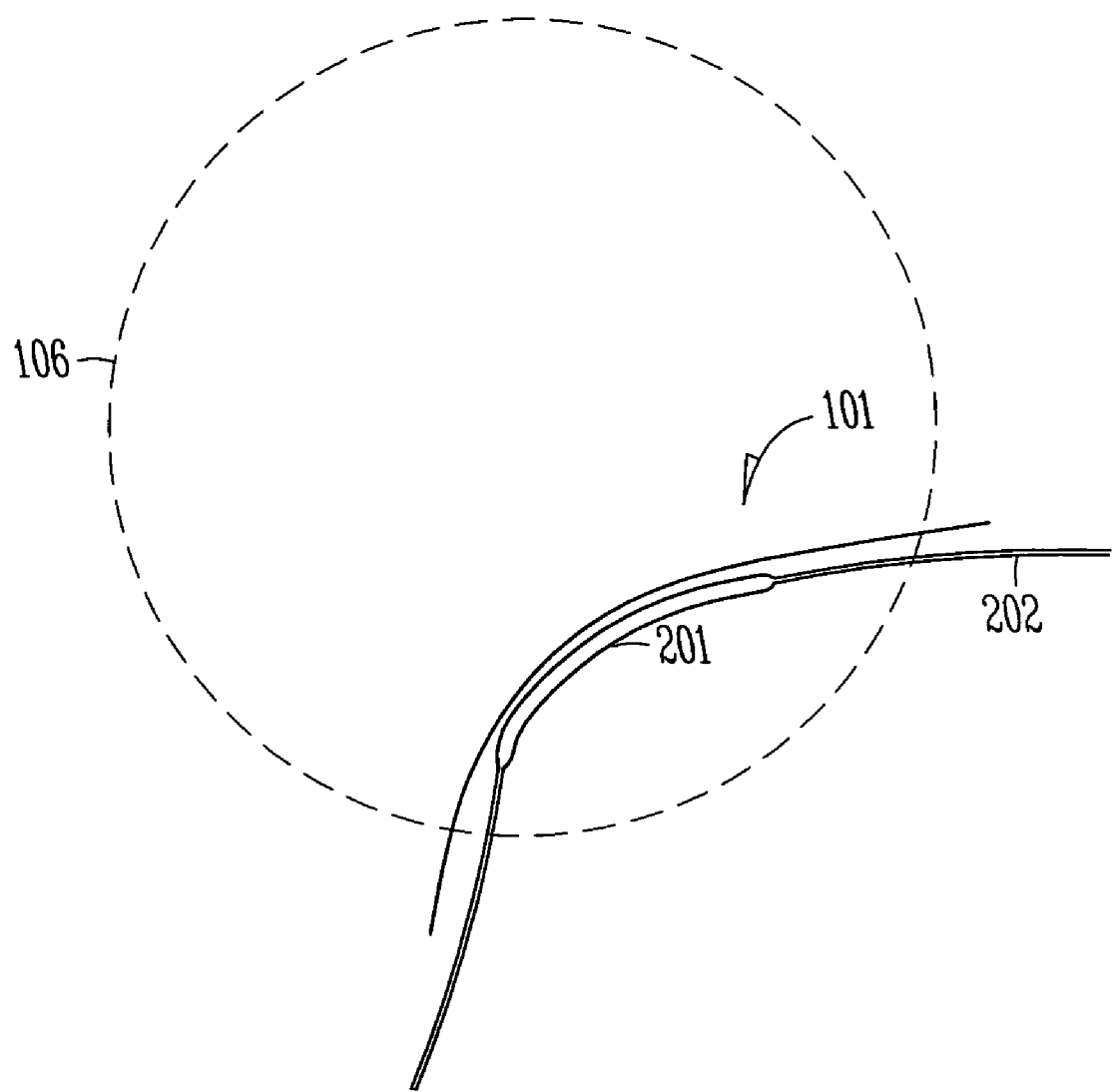
FIG. 2 is a schematic drawing that shows the circular area 106 near the right shoulder of FIG. 1 in more detail.

FIG. 2 is a schematic drawing that shows the circular area 106 near the right shoulder of FIG. 1 in more detail. In this example, a tube 101 includes a flexible sensing element 201 and a non-sensing conduit 202. The flexible sensing element 201 and the non-sensing conduit each include a longitudinal lumen that is connected to a similar longitudinal lumen of the other. This allows the flowable substance carried within the lumen of each to flow between the flexible sensing element 201 and the non-sensing conduit 202. In certain examples, at least one of the lumens includes a diameter of less than 1 inch. In certain examples, at least one of the lumens includes a diameter of less than 1 millimeter.

In this example, the flexible sensing element 201 includes a flexible elastic tube or ribbon that expands when filled or inflated with the flowable substance, such as the gas, liquid, gel, or the like. In this example, the local volume or pressure of the flowable substance carried within a lumen of the flexible sensing element 201 changes when the flexible sensing element 201 is bent or twisted. The non-sensing conduit 202, in this example, is configured such that does not substantially change the volume or pressure of the flowable substance carried within its lumen. Therefore, movement of the shoulder joint causes the flexible sensing element 201 to be bent, twisted, or elongated, and the resulting change in its interior flowable substance pressure travels through the non-sensing conduit 202 to the ambulatory transducer unit 102.

In the example of FIG. 2, the flexible sensing element 201 and the non-sensing conduit 202 are configured such that the transducer in the ambulatory transducer unit 102 is less sensitive to the longitudinal axial bending or twisting of the non-sensing conduit 202 than to that of the flexible sensing element 201. This can be accomplished by making the flexible sensing element 201 more flexible and compressible than non-sensing conduit 202 of the tube 101. In such an example, only bending or twisting movement of the flexible sensing element 201 significantly impacts flow within the tube 101, such that body position or motion information from particularized remote locations (e.g., the right shoulder) across the body can be conveyed to the convergent ambulatory transducer unit 102.

In an example, a fluid pressure or flow amplifier or attenuator can be optionally included, such as at or near a pressure or flow transducer of the ambulatory transducer unit 102 or located elsewhere, or in the path between any flexible sensing element 201 and the ambulatory transducer unit 102. This can be useful to amplify or attenuate the change in pressure or flow produced by the flexible sensing element 201, such as to make it easier to detect by the pressure or flow transducer of the ambulatory transducer unit 102 or elsewhere. A fluid pressure or flow amplifier or attenuator can utilize a widening or narrowing of the interior diameter of the non-sensing conduit 201, as an illustrative example.

In a particular example useful to construct a prototype to establish proof-of-concept, thin-walled plastic heat-shrink tubing can be used for the flexible sensing elements 201 and thicker-walled, but still flexible, plastic tubing can be used for the non-sensing conduits 202. The flexible sensing element 201 can be joined to the non-sensing conduit 202 such that the gas, liquid, gel, or other flowable substance can move contiguously from the lumen of one to the lumen of the other.

Figure 3:
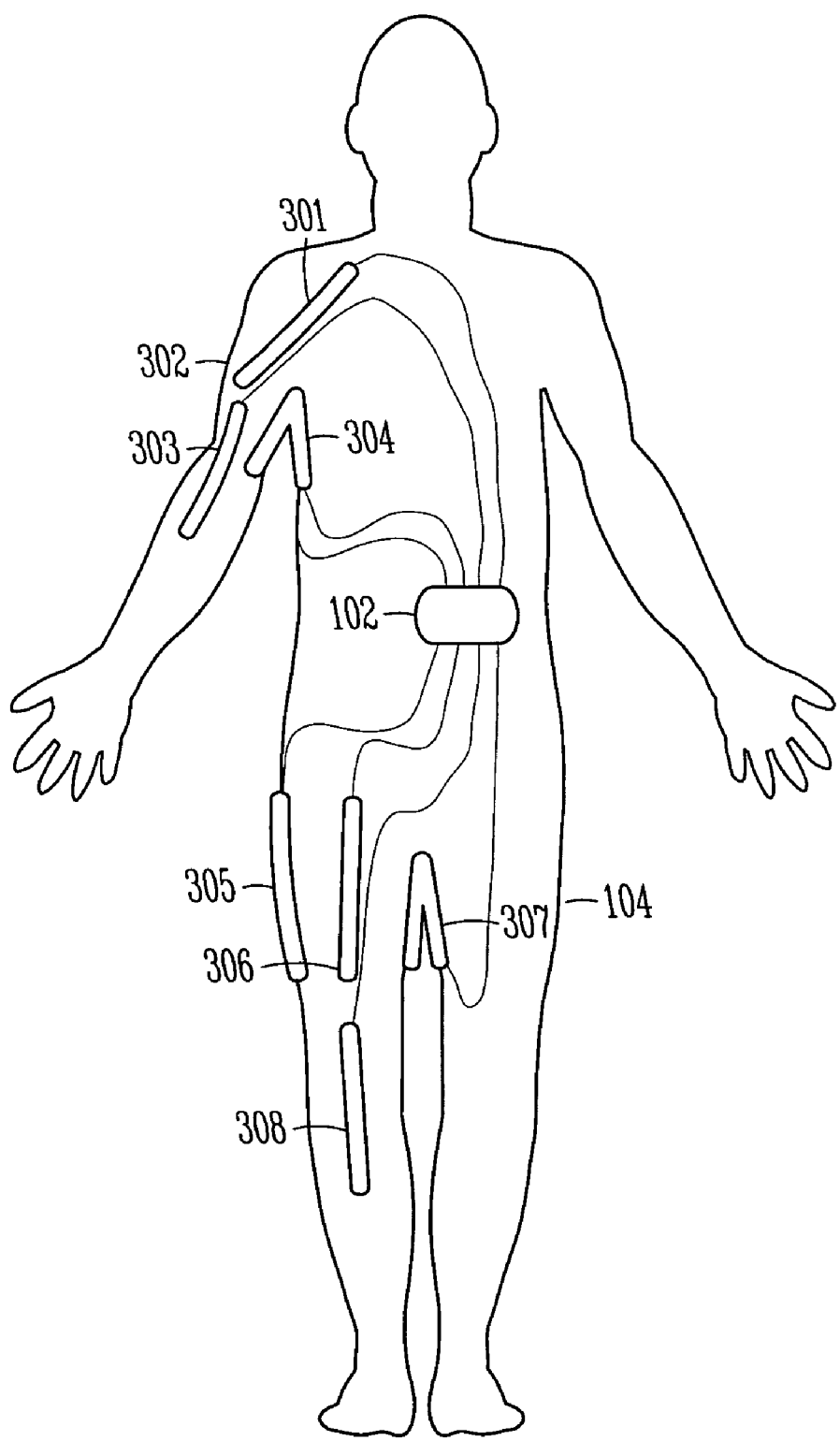
FIG. 3 is a schematic drawing illustrating generally another example of a system for collecting body position and motion information.

FIG. 3 is a schematic drawing illustrating generally another example of a system for collecting body position and motion information. The example can be used to construct a prototype to test the relationships between joint angles and tube pressures at the ambulatory transducer unit 102. In this example, a flexible sensing element 301 is located on the front of the right shoulder 301. A flexible sensing element 302 is located on the back of the elbow (hidden from view). A flexible sensing element 303 is located at the front of the elbow. A flexible sensing element 304 is located underarm. A flexible sensing element 305 is located on an outside seam of the hip on the right leg. A flexible sensing element 306 is located on the front of the right leg across the hip. A flexible sensing element 307 is located on the inside seam of the hip. A flexible sensing element 308 is located on the front of the right knee. Locating flexible sensing elements on two opposing sides of the same joint may be somewhat redundant, however, since there are different amounts of body tissue between the joint and differently located inner and outer body surfaces, combining information on the same joint motion from two different surface locations could improve measurement accuracy. In certain examples, a particular joint may be associated with at least two different flexible sensing elements that are generally located in parallel directions to each other. In certain examples, a particular joint may be associated with at least two different flexible sensing elements that are generally located orthogonal to each other. In certain examples, a particular joint may be associated with at least two different flexible sensing elements that are arbitrarily oriented non-parallel and non-orthogonal to each other.

There are numerous suitable ways by which the tubes 101 can be coupled to or worn by the subject, including ways of attaching the tubes 101 to a garment or other wearable structure. As an example, a prototype can be constructed by fitting the tubes 101 into respective flexible plastic mesh channels that can be attached to a flexible, elastic garment. The tubes 101 can stretch and move within such respective mesh channels, so as to not limit the mobility of the person wearing the garment. However, the mesh channels will generally keep the tubes 101 in reasonable conformity with body contour, which is useful for measuring joint position or motion. In this prototype example, some directions of joint motion will bend the corresponding flexible sensing element, thereby generally increasing the pressure of the flowable substance within that flexible sensing element. Other directions of joint motion will straighten the flexible sensing element, thereby generally reducing the pressure of the flowable substance within that flexible sensing element. Calibration for specific joints or specific flexible sensing elements can be performed before analyzing subsequent transduced signals from the flexible sensing elements to infer body position or motion.

Figure 4A:
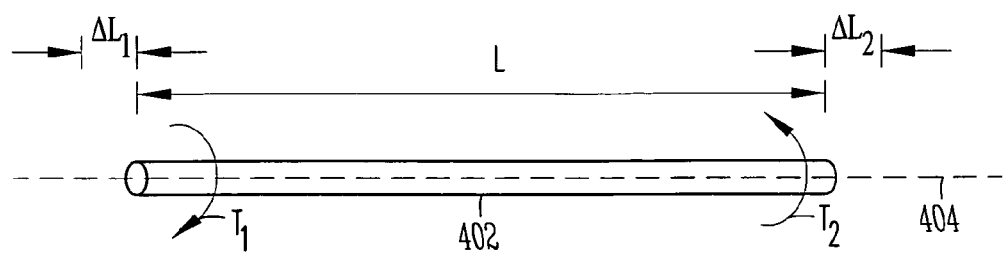
FIG. 4A is a drawing of an example of a flexible sensing element comprising a elongated tube filled with a flowable substance.

FIG. 4A is a drawing of an example of a flexible sensing element 402 comprising a elongated tube filled with a flowable substance, such as described above. In this example, the elongated tube of the flexible sensing element 402 defines a longitudinal axis 404, such as shown in FIG. 4A.

Figure 4B:
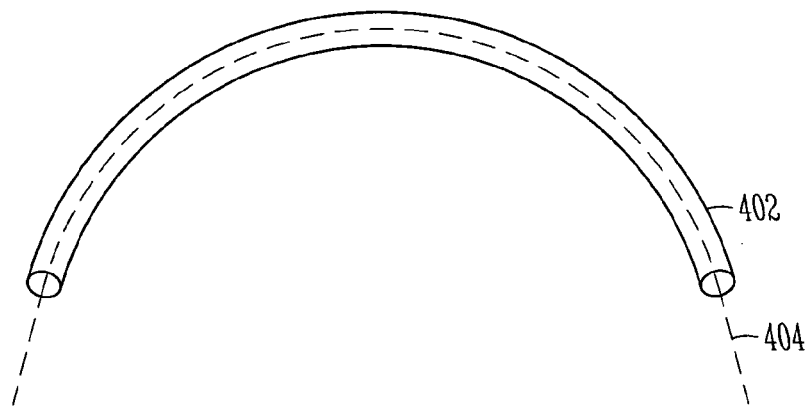
FIG. 4B shows example of a longitudinal axial bending of a flexible sensing element.

FIG. 4B shows example of a longitudinal axial bending of the flexible sensing element 402. Such bending can cause a change in pressure of the fluid that the sensing element 402 contains. The change in pressure can be either with respect to a condition in which the flexible sensing element 402 is straight (such as shown in FIG. 4A), or with respect to a baseline condition in which the flexible sensing element 402 is already somewhat bent (such as shown in FIG. 4B, with further bending causing a change in pressure). FIG. 4A also depicts a possible elongation of the length, L, such as by one or both of $\Delta L_1$ or $\Delta L_2$, either of which can also cause a change in pressure of the fluid contained in the flexible sensing element 402. FIG. 4A also depicts a possible twisting of the flexible sensing element such as in the direction of one or both of $T_1$ or $T_2$ as shown (or vice-versa), either of which can also cause a change in pressure of the fluid contained in the flexible sensing element 402. Similarly, a change in pressure of the fluid contained in the flexible sensing element 402 can be caused by a combination of longitudinal axial bending, twisting, or elongation, such as described above.

Figure 4C:
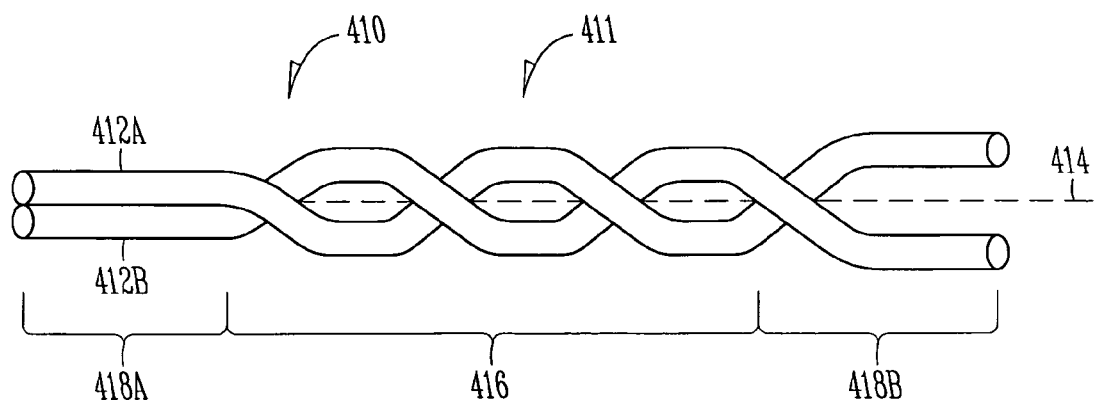
FIG. 4C is a drawing of an example of a braided, woven, or twisted flexible sensing element.

FIG. 4C is a drawing of an example of a braiding, weaving, or twisting of two or more strands 412A-B of either of a flexible sensing element 410 or a non-sensing conduit 411 (e.g., located between the flexible sensing element 410 and an ambulatory transducer unit, such as described above). The braided, woven, or twisted flexible sensing element 410 or non-sensing conduit 411 also defines a longitudinal axis 414, as shown, which can also be bent in a similar manner to axis 404 shown in FIG. 4B. For a flexible sensing element 410, such bending will cause a change in pressure from a straight or bent baseline condition. Thus, the flexible sensing element 410 can bent, twisted, elongated, or the like, such as described above with respect to FIG. 4A, to cause a change in pressure from a straight or bent baseline condition.

In certain examples, the flexible sensing element 410 or the non-sensing conduit 411 can include a central braided, woven, or twisted portion 416 and end portions 418A-B that are not braided, woven, or twisted. The braided, woven, or twisted portion 416 can add extra strength to the flexible sensing element 410 or the non-sensing conduit 411, such as for undergoing bending, twisting, or elongation, such as described above. The braided, woven, or twisted portion 416 can help reduce or avoid kinking, such as in response to a longitudinal axial bending. Such kinking could potentially distort or block the pressure response of a non-woven flexible sensing element 402 or the fluid communication of the non-sensing conduit 411, such as resulting from a longitudinal axial bending. The multiple strands 412A-B can also offer some redundancy in sensing, because they can be similarly located with respect to a particular joint, or in fluid communication to an ambulatory transducer unit.

The degree of braiding, weaving, or twisting of a flexible sensing element 410 or a non-sensing conduit 411 can be measured by a "wrap angle," which can be conceptualized as an angle at which a strand crosses the longitudinal axis 414, taken with respect to the longitudinal axis 414. Thus, as the number of windings per unit length of the portion 416 are increased, the windings become more perpendicular to the longitudinal axis, and the wrap angle increases. As the number of windings per unit length of the portion 416 are decreased, the windings become less perpendicular to the longitudinal axis, and the wrap angle decreases.

Without being bound by theory, as the wrap angle increases (e.g., more windings per unit length), the portion 416 can generally accommodate more longitudinal axial bending, and as the wrap angle decreases (e.g., fewer windings per unit length), the portion 416 can generally accommodate more elongation or twisting. The flexible sensing element 410 or the non-sensing conduit 411 can be configured to provide a desired wrap angle, such as to provide the desired physical ability to accommodate elongation, twisting, or longitudinal axial bending, or to provide the desired sensing response, the desired non-sensing fluid communication response, or the desired relation between the sensing and non-sensing responses to the same. In certain examples, a different wrap angle is provided near the center of the portion 416 than for regions of the portion 416 that are near the ends 418A-B, such as to accommodate more elongation or twisting near the ends 418A-B and to accommodate more longitudinal axial bending near the center of the portion 416.

Thus, the wrap angle for some portions of the flexible sensing element 410, or for a non-sensing conduit 411 attached to the flexible sensing element 410, can be relatively more or less than the wrap angle of other portions of the flexible sensing element 410, or the non-sensing conduit 411 attached to the flexible sensing element 410. This includes the possibility that some portions of the flexible sensing element 410 or the non-sensing conduit 411 may not be braided, woven, or twisted at all. Braiding, weaving, or twisting portions of a flexible sensor element 410 or of a non-sensing conduit 411 at different wrap angles can change the relative responses of portions of the flexible sensing element 410 or the non-sensing conduit 411 to bending, twisting, or elongation. For example, a portion of a flexible sensing element 410 that is braided, woven, or twisted with a certain wrap angle may be less likely to kink and thus provide a more smoothly-continuous measurement over a wider range of bending. As another example, a non-sensing conduit 411 that is braided, woven, or twisted conduit with a high wrap angle may be more able to move without distorting the desired conduction of the pressure signal from a flexible sensing element to a remote transducer. In the example of FIG. 4C, the central portion 416 of a sensor is braided, woven, or twisted and the end points of the sensor 418A-B are not. Similarly, either the flexible sensing element 410 or the non-sensing conduit 411 can be otherwise strengthened, such as to inhibit kinking. In certain examples, this can be accomplished by using braided, woven, or twisted strengthening filaments, which can be wrapped around the flexible sensing element 410 or the non-sensing conduit 411 at a desired wrap angle, or incorporated into the tubular wall of the flexible sensing element 410 or the non-sensing conduit 411 at a desired wrap angle.

Figure 5A:
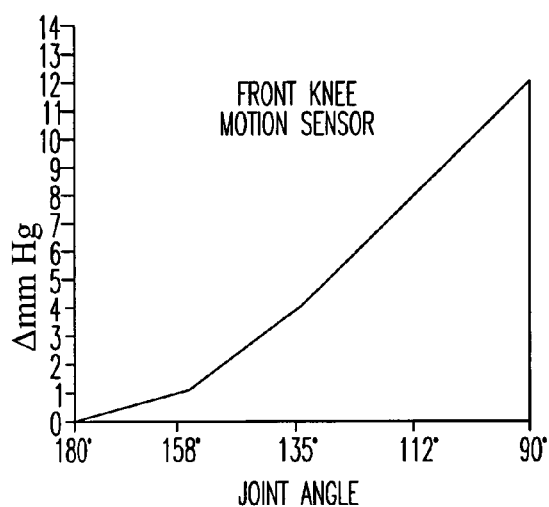
FIGS. 5A, 5B, 5C, and 5D are examples of graphs of change in pressure (in millimeters of mercury) vs. joint angle, providing some preliminary data obtained from the lower body flexible sensing elements of the prototype described above with respect to FIG. 3.
Figure 5B:
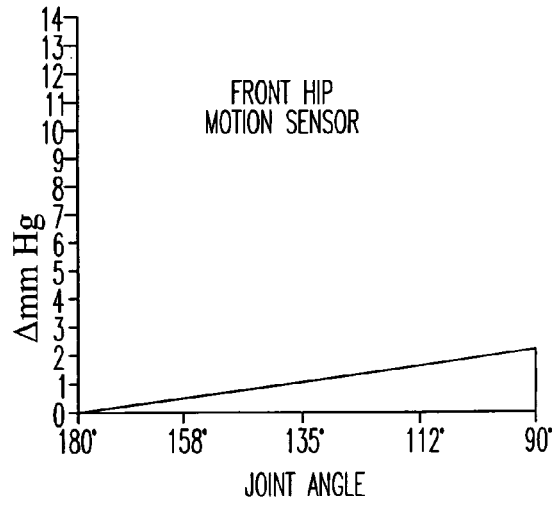
Figure 5C:
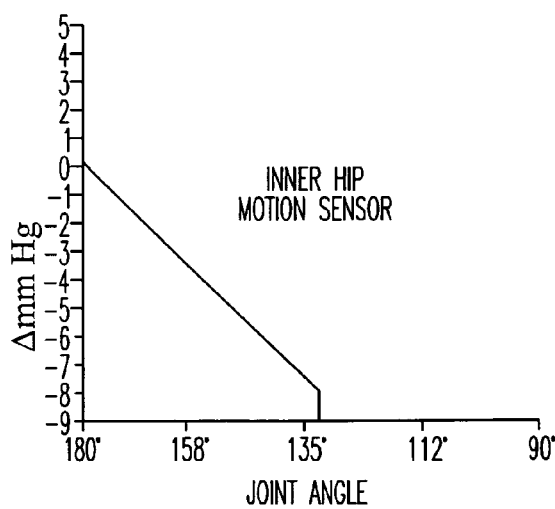
Figure 5D:
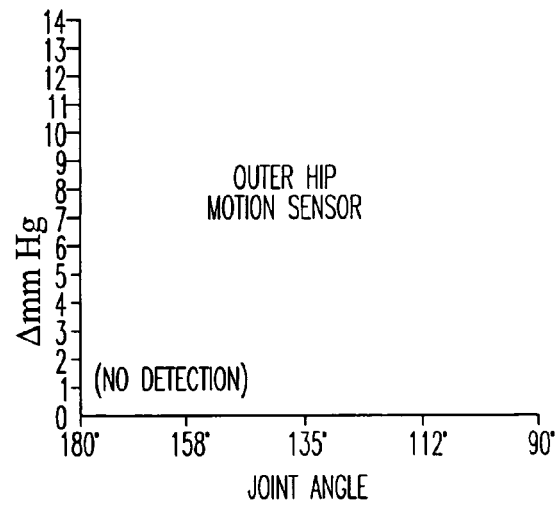

FIGS. 5A, 5B, 5C, and 5D are examples of graphs of change in pressure (in millimeters of mercury) vs. joint angle, providing some preliminary data obtained from the lower body flexible sensing elements of the prototype described above with respect to FIG. 3. In this example, however, the ambulatory transducer unit 102 was omitted. Instead, the pressure of the flowable substance (in this case, the tubes 101 were inflated with air) was individually transduced at an abdominal location using a blood pressure gauge. FIG. 5A shows change in pressure vs. joint angle for the front knee flexible sensing element 308. FIG. 5B shows change in pressure vs. joint angle for the front hip flexible sensing element 306. FIG. 5C shows change in pressure vs. joint angle for the inner hip flexible sensing element 307. FIG. 5D shows a change in pressure vs. joint angle for the outer hip flexible sensing element 305.

Figure 6A:
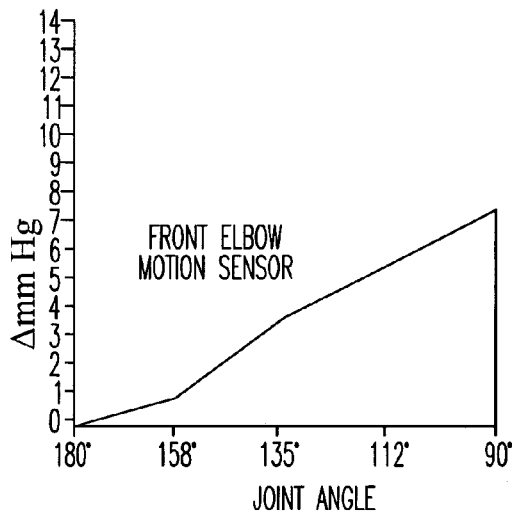
FIGS. 6A, 6B, 6C, and 6D are examples of graphs of change in pressure (in millimeters of mercury) vs. joint angle, providing some preliminary data obtained from the upper body flexible sensing elements of the prototype described above with respect to FIG. 3.
Figure 6B:
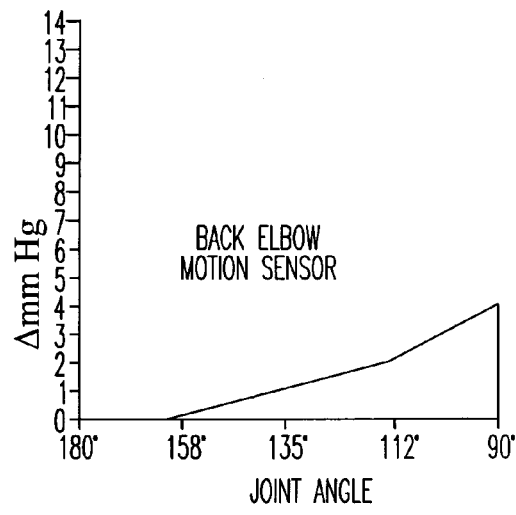
Figure 6C:
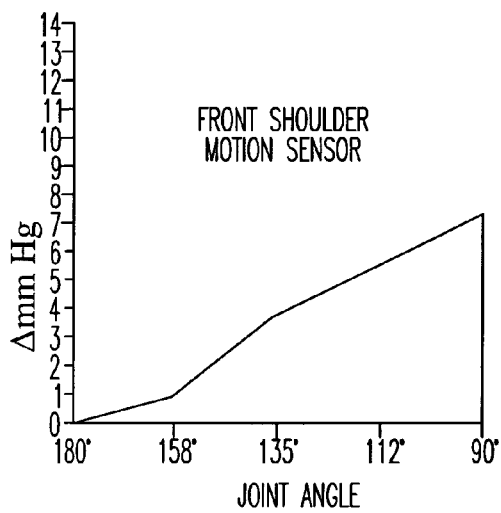
Figure 6D:
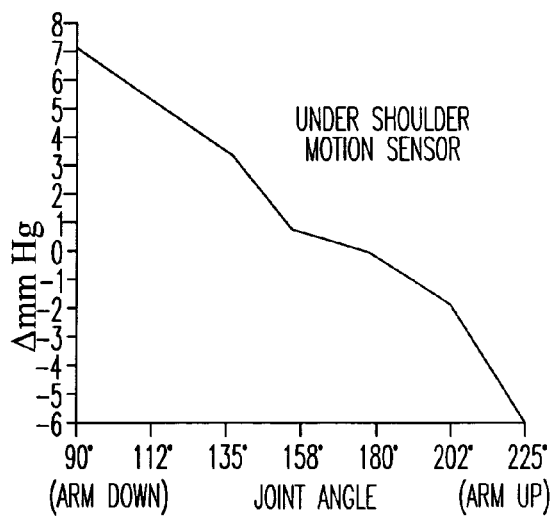

FIGS. 6A, 6B, 6C, and 6D are examples of graphs of change in pressure (in millimeters of mercury) vs. joint angle, providing some preliminary data obtained from the upper body flexible sensing elements of the prototype described above with respect to FIG. 3. In this example, however, the ambulatory transducer unit 102 was omitted. Instead, the pressure of the flowable substance (in this case, the tubes 101 were inflated with air) was individually transduced at an abdominal location using a blood pressure gauge. FIG. 6A shows change in pressure vs. joint angle for the front elbow flexible sensing element 303. FIG. 6B shows change in pressure vs. joint angle for the back elbow flexible sensing element 302. FIG. 6C shows change in pressure vs. joint angle for the front shoulder flexible sensing element 301. FIG. 6D shows a change in pressure vs. joint angle for the underarm (under shoulder) flexible sensing element 304.

The preliminary data in FIGS. 5A, 5B, 5C, 5D, 6A, 6B, 6C, and 6D shows that, in principle, it is possible to obtain joint position or motion data using pressure sensing from worn flexible sensing elements. Although the data is not perfectly linear or uniform, at least one flexible sensing element on each joint yielded a monotonic relationship between joint angle and pressure. These early results strongly suggest that, the present systems and methods can indeed provide useful information from which to infer body position or motion.

Although the above description has emphasized, among other things, certain hydraulic or pneumatic examples in which the measured parameter of the flowable substance includes pressure, in certain examples, the measured parameter of the flowable substance includes a flow or volume change. For example, the tubes 101 can be configured in a loop through which the flowable substance is pumped, and a change in the flow of the flowable substance can be transduced to provide information about body position or motion due to bending or twisting of the flexible sensing elements. In certain examples, it can be useful to use a flowable substance that is relatively incompressible, which can sometimes be expressed in terms of the bulk modulus of elasticity of the flowable substance. In certain examples in which the measured parameter of the flowable substance includes pressure, it can be useful to also include an atmospheric pressure sensor, such as can be included in the ambulatory transducer unit 102 or elsewhere, for example, to account for any effect of changing atmospheric pressure on the pressure change measurements. It certain examples, the flexible sensing elements 201 or the non-sensing elements 202 can be made transparent or translucent. In certain examples, the flowable substance carried within the flexible sensing elements 201 and the non-sensing elements 202 can be made colored or luminescent. In certain examples, the ambulatory transducer unit 102 can communicate wirelessly or otherwise (e.g., via RF, inductive, IR, or other communication link) with a local or remote computer (e.g., over a communication network) such as for monitoring or to provide a user interface. Such communication can be unidirectional or bidirectional. In certain examples, the wearable garment or the ambulatory transducer unit 102 can include or be coupled to one or more other ambulatory physiological monitors, such as a heart rate monitor, a blood pressure monitor, an accelerometer, a pedometer, or the like, and information from one or more such other ambulatory physiological monitors can also be communicated wirelessly or otherwise to a local or remote computer for analysis or display.

Although the above examples have emphasized, among other things, certain examples in which fluid communication of a flowable substance is used to communicate information between various flexible sensing elements 201 and respective pressure transducers located in a combined ambulatory transducer unit 102, in certain examples, the pressure transducers can be located at the flexible sensing elements 201, and instead of the tubes 101, electrical signals can be conveyed via wires or wirelessly from such locations to a combined ambulatory signal storage or processing unit instead of to the combined ambulatory transducer unit 102. In certain examples, such wireless communication can use inductive or RF links, can use the body as a conductor, or can even use ultrasonic rather than electrical communication.

In certain examples, the devices and techniques described can offer certain advantages over other approaches. For example, they permit continuous tracking of a person's posture or movement or the like even when a line of sight is obscured, which is an advantage over an approach that uses external video imaging of active or passive, fiducial markers on the body. As another example, it can be made very portable and even ambulatory, which is an advantage over an approach that uses external video imaging and that uses one or more cameras or the like. As another example, it permits measurement of both large-scale and small scale motion simultaneously, which can also be an advantage over an approach that uses external video imaging. As another example, it permits high mobility over the person, due to the use of a flexible garment structure, which can be an advantage over an approach that uses contiguous sensors with more rigid components. As another example, it can avoid the cumbersome nature of an approach that uses transducers located all over the body, such as by allowing fluid communication with the shared ambulatory transducer unit 102. As another example, it can provide a potentially washable garment with a single detachable electronic component (e.g., the ambulatory transducer unit 102), as opposed to an approach that disperses electronic components across the body (although this is also an option with the current approach). As another example, it can avoid cumbersome multiple transmitting or receiving components that are spread out all over the body, as opposed to an approach that uses multiple transmitters distributed across the body. As another example, it can avoid limitations due to transmission range or interference, as opposed to an approach that uses multiple wireless transmitters. Not all examples of the present devices and techniques need provide all of these advantages.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:
1. An apparatus comprising:
an external flexing sensing element, configured to be externally coupled to or externally worn on a human or animal body, the sensing element providing an indication of an external longitudinal axial bending, twisting, or elongation due to movement of at least one body part, the sensing element comprising a flexible elongate member, the flexible elongate member comprising a lumen carrying a flowable substance comprising at least one of a liquid, a gas, or a gel; and
a transducer, in flowable substance communication with the lumen of the sensing element, the transducer configured to transduce an indication of the longitudinal axial bending, twisting, or elongation of the sensing element into at least one output indication of body part movement to be provided to a user or a device.
2. The apparatus of claim 1, comprising:
a plurality of the external flexing sensing elements, comprising a first sensing element and a second sensing element, the first and second sensing elements comprising respective external flexible elongate members comprising respective lumens carrying the flowable substance; and
a plurality of the transducers respectively are in flowable communication with the first and second sensing elements, the transducer configured to transduce indications of the longitudinal axial bending of the first and second sensing elements into the at least one output indication of a change in external angle between two parts or surfaces of a human or animal body.
3. The apparatus of claim 2, comprising an external garment with which the first and second sensing elements are integrated.
4. The apparatus of claim 3, wherein the garment comprises a compressive fabric to hold the first and second sensing elements externally against the body.
5. The apparatus of claim 2, wherein the first sensing element is generally parallel to the second sensing element.
6. The apparatus of claim 2, wherein the first sensing element is generally orthogonal to the second sensing element.
7. The apparatus of claim 1, wherein the flowable substance is a gas.
8. The apparatus of claim 1, comprising a coupling device, configured to couple the sensing element to the body.
9. The apparatus of claim 1, wherein the transducer is configured to transduce an indication of at least one of flow, volume, or pressure of the flowable substance, arising from the longitudinal axial bending, twisting, or elongation of the sensing element, into an electrical or optical signal representing the indication of body part movement.
10. The apparatus of claim 9, comprising at least one flowable substance conduit, coupled to the lumen, wherein the transducer is in flowable substance communication with the lumen via the conduit, and wherein the at least one conduit and the sensing element are configured such that the transducer is less sensitive to the longitudinal axial bending, twist- ing, or elongation of the at least one conduit than to the corresponding longitudinal axial bending, twisting, or elongation of the sensing element.

11. The apparatus of claim 9, wherein the transducer is configured to transduce an indication of pressure of the flowable substance, arising from the longitudinal axial bending, twisting, or elongation of the sensing element, into an electrical signal representing the indication of body part movement.

12. The apparatus of claim 1, wherein the sensing element is inflatable.

13. The apparatus of claim 1, wherein the first sensing element and the at least one conduit form a flowable substance conduction loop.

14. The apparatus of claim 1, wherein the lumen comprises a diameter of less than 1 inch.

15. The apparatus of claim 1, wherein the lumen comprises a diameter of less than 1

16. The apparatus of claim 1, comprising a number of sensing elements that is selected to represent movement of joints distributed throughout the body.

17. The apparatus of claim 1, wherein at least a portion of the sensing element comprises multiple braided, woven, or twisted strands.

18. The apparatus of claim 1, wherein the sensing element is configured to transducer an external longitudinal axial bending into an indication of a change in external angle between two parts or surfaces of a human or animal body.

19. A method comprising:
externally sensing an external longitudinal axial bending, twisting, or elongation of an external flexible elongate member sensing element that is externally coupled to or worn on a human or animal body, the sensing including using a flowable substance carried by a lumen of the flexible elongate member, the flowable substance comprising at least one of a liquid, a gas, or a gel; and
externally transducing an indication of the longitudinal axial bending, twisting, or elongation of the sensing element into at least one output indication of body part movement to be provided to a user or a device.

20. The method of claim 19, comprising:
externally sensing a longitudinal axial bending, twisting, or elongation of a plurality of the external flexible elongate member sensing elements comprising a first sensing element and a second sensing element; and
communicating the flowable substance from the plurality of the flexible elongate member sensing elements to at least one transducer that is in flowable communication with at least one of the first and second sensing elements for performing the transducing.

21. The method of claim 20, wherein the sensing comprises using first and second sensing elements that are generally externally located in parallel to each other.

22. The method of claim 20, wherein the sensing comprises using first and second sensing elements that are generally externally located orthogonal to each other.

23. The method of claim 19, wherein the sensing comprises sensing at least one of a flow or a volume of the flowable substance.

24. The method of claim 19, wherein the sensing comprises sensing a pressure of the flowable substance.

25. The method of claim 19, wherein the sensing comprises using at least one of a braided, woven, or twisted flexible elongate member.

26. The method of claim 19, wherein externally transducing an indication of the longitudinal axial bending, twisting, or elongation of the sensing element comprises externally transducing an indication of the longitudinal axial bending into at least one output indication of a change in external angle between two parts or external surfaces of a human or animal body.

27. An apparatus comprising:
means for externally sensing an external longitudinal axial bending, twisting, or elongation of an external flexible elongate member sensing element that is externally coupled to or externally worn on a human or animal body, the sensing including using a flowable substance carried by a lumen of the flexible elongate member, the flowable substance comprising at least one of a liquid, a gas, or a gel; and
means for externally transducing an indication of the longitudinal axial bending, twisting, or elongation of the sensing element into at least one output indication of body part movement to be provided to a user or a device.

28. The apparatus of claim 27, wherein the means for externally transducing the indication of the longitudinal axial bending, twisting, or elongation of the sensing element into at least one output indication of body part movement to be provided to a user or a device comprises a means for externally transducing an indication of longitudinal axial bending into at least one output indication of a change in external angle between two parts or external surfaces of a human or animal body.

* * * * *

UNITED STATES PATENT AND TRADEMARK OFFICE
CERTIFICATE OF CORRECTION

| | | |
|---|---|---|
| PATENT NO. | : 7,980,141 B2 | Page 1 of 1 |
| APPLICATION NO. | : 12/080164 | |
| DATED | : July 19, 2011 | |
| INVENTOR(S) | : Robert A. Connor et al. | |

It is certified that error appears in the above-identified patent and that said Letters Patent is hereby corrected as shown below:

In column 13, line 16, in Claim 14, delete "1inch." and insert -- 1 inch. --, therefor.

In column 13, line 18, in Claim 15, after "1" insert -- millimeter. --.

Signed and Sealed this
First Day of November, 2011

David J. Kappos
*Director of the United States Patent and Trademark Office*